United States Patent [19]

Russell-Jones

[11] Patent Number: 5,863,900
[45] Date of Patent: Jan. 26, 1999

[54] LHRH ANTAGONISTS

[75] Inventor: Gregory John Russell-Jones, Middle Cove, Australia

[73] Assignee: Biotech Australia Pty., Ltd., Roseville, Australia

[21] Appl. No.: 537,941

[22] PCT Filed: May 20, 1995

[86] PCT No.: PCT/AU94/00262

§ 371 Date: Jan. 16, 1996

§ 102(e) Date: Jan. 16, 1996

[87] PCT Pub. No.: WO94/28015

PCT Pub. Date: Dec. 8, 1994

[30] Foreign Application Priority Data

May 20, 1993 [AU] Australia ..................... PL 8880

[51] Int. Cl.$^6$ .......................... A61K 38/00; A61K 38/02; C07K 5/00; C07K 7/00
[52] U.S. Cl. .................... 514/15; 514/2; 514/12; 514/13; 514/14; 530/402; 530/313
[58] Field of Search .................. 514/2, 12, 13, 514/14, 15; 530/402, 313

[56] References Cited

FOREIGN PATENT DOCUMENTS

| | | |
|---|---|---|
| 65289/86 | 8/1989 | Australia . |
| 32637/89 | 5/1992 | Australia . |
| 8702251 | 4/1987 | WIPO ........................ A61K 39/44 |
| WO 91/19737 | 12/1991 | WIPO . |

OTHER PUBLICATIONS

A. Ljungqvist et al., "Antagonist of LHRH Superior to Antide; Effective Sequence/Activity Relationships", Tetrahedron, vol. 46, No. 9, 1990, pp. 3297–3304.

M. Matsuda et al., "Dissociation of Tetanus Neurotoxin into Two Polypeptide Fragments", Biochemical and Biophysical Research Communications, vol. 57, No. 54, 1974, pp. 1257–1262.

K. Sandvig et al., "Rapid Entry of Nicked Diphtheria Toxin into Cells at Low pH", The Journal of Biological Chemistry, vol. 256, No. 17, 1981, pp. 9068–9076.

A. Schally et al., "Gonadotropin–Releasing Hormone: One Polypeptide Regulates Secretion of Luteinizing and Follicle–Stimulating Hormones", Science, vol. 173, No. 3998, Aug., 1971, pp. 1036–1038.

E. Loumaye et al., "Binding Affinity and Biological Activity of Gonadotropin–Releasing Hormone Agonists in Isolated Pituitary Cells", Endocrinology, vol. 111, No. 3, 1982, pp. 730–736.

M. Perrin et al., "Radioligand Assay for Gonadotropin–Releasing Hormone: Relative Potencies of Agonists and Atagonists", Endocrinology, vol. 106, No. 4, 1980, pp. 1289–1295.

M. Eisenberger et al., "Gonadotropin Hormone—Releasing Hormone Analogs for the Treatment of Prostatic Cancer", Drugs of Today, vol. 24, No. 4, 1988, pp. 241–248.

E. Crawford et al., "Luteinizing Hormone Releasing Hormone Analogues in the Treatment of Prostate Cancer", Endocrine Therapies in Breast and Prostate Cancer, 1988, pp. 25–38.

M. Karten et al., "Gonadotropin–Releasing Hormone Analog Design. Structure–Function Studies Toward the Development of Agonists and Antagonists: Rationale and Perspective", Endocrine Reviews, vol. 7, 1988, pp. 44–66.

F. Schmidt et al., "A Potent Antagonist of LHRH, Produces Transient Edema and Behavioral Changes in Rats", Contraception, Mar. 1984, vol. 29, No. 3, pp. 283–289.

J. Leal et al., "Prolonged Duration of Gonadotropin Inhibiti9on by a Third Generation GNRH Antagonist", Journal of Clinical Endocrinology and Metabolism, vol. 67, No. 6, 1988, pp. 1325–1327.

U. Habenight et al., "Effect of the New Potent LHRH Antagonist Antide", J. Steroid Biochem. Molec. Biol., vol. 37, No. 6, 1990, pp. 937–942.

R. McLachlan et al., "Clinical Aspects of LHRH Analogues in Gynaecology: A Review", British Journal of Obstetrics and Gynaecology, May 1986, vol. 93, pp. 431–454.

P.G. Farnworth et al., "Effects of 31 Kilodalton Bovine Inhibin on Follicle–Stimulating Hormone and Luteinizing Hormone in Rat Pituitary Cells in Vitro: Actions under Basal Conditions", Endocrinology, vol. 122, No. 1, 1988, pp. 207–213.

G. Russell–Jones, "Oral Delivery of Therapeutic Proteins and Peptides by the Vitamin $B_{12}$ Uptake System", Peptide–Based Drug Design: Controlling Transport and Metabolism, Chapter 8, 1994.

A. Phillips et al., "Evaluatin of the Anaphylactoid Activity of a New LHRH Antagonist", Life Sciences, vol. 43, No. 11, 1988, pp. 883–888.

A. Ljungqvist et al., "Antide and Related Antagonists of Luteinizing Hormone Release with Long Action and Oral Activity", Proc. Natl. Acad. Sci. USA, vol. 85, Nov. 1988, pp. 8236–8240.

M.E. Anderson et al., "Dynamic State of Glutathione in Blood Plasma", Journal of Biological Chemistry, vol. 255, No. 20, Oct. 1980, pp. 9530–9533.

*Primary Examiner*—Avis M. Davenport
*Attorney, Agent, or Firm*—Foley & Lardner

[57] ABSTRACT

The present invention provides novel LHRH antagonists and complexes between these antagonists and VB12. The present invention is particularly useful for the oral administration of LHRH antagonists. The antagonists of the invention are selected from the group consisting of ANTIDE-1, ANTIDE-2 and ANTIDE-3.

15 Claims, 4 Drawing Sheets

LHRH ANTAGONISTS

FIELD OF THE INVENTION

The present invention relates to LHRH antagonists and to the systemic and oral delivery of the antagonists by administration of a complex comprising the antagonists linked to vitamin B12 (VB12) or an analogue thereof. More particularly, the invention relates to methods for the synthesis of these complexes.

BACKGROUND OF THE INVENTION

Hypothalamic gonadotrophin releasing hormone (GnRH, also known as luteinizing hormone releasing hormone, LHRH) mediates the regulation of pituitary gonadotrophin synthesis and secretion. Since the initial isolation of LHRH by Schally et al. (1971) numerous analogues have been synthesized, which may be classified according to their acute effects on gonadotrophin release, as either agonists (with enhancement of release) or antagonists, (with inhibition of release). The agonists are characterised by an increase in binding affinity to pituitary LHRH receptors (Loumay et al, 1982, Perrin et al. 1980) and by increased resistance to the proteolytic degradation that rapidly removes native LHRH.

The observation that these potent analogues can induce potentially reversible medical castration has provided a new approach to the treatment of various gonadotrophin dependent disorders, particularly hormone dependent prostate and breast cancer. Two distinct phases in the induction of castration occur. Initially the analogue stimulates the pituitary-gonadal axis causing a transient increase in gonadotrophin and sex steroid secretion in the first two weeks or so. After this period there is a down regulation of pituitary LHRH receptors with subsequent decline in gonadotrophin and sex steroid secretion. The initial stimulation is a substantial drawback to the use of agonists in the treatment of prostatic malignancy as the initial stimulation of testosterone can produce a painful flare of the disease with consequent adverse clinical effects (Eisenberger and Abrams, 1988, Crawford and Davis, 1988). By contrast the first successful synthesis of LHRH antagonists should be advantageous in avoiding the initial flare. First attempts at the production of antagonists led to compounds characterised by undesirable histamine release (Karten and Rivier, 1986, Schmidt et al., 1984, Phillips et al ., 1988). However new antagonists have been developed characterised by improved potency and much less histamine releasing potential eg. Karten and Rivier, 1986. One of the most potent antagonists described to date is the analogue N-Ac-D-Nal(2), D-Phe (pCl), D-Pal (3), Ser, Lys (Nic), D-Lys(Nic), Leu, Lys(iPr), Pro, D-Ala-NH2 (ANTIDE), synthesized by Folkers and Bowers. It is highly potent in rats in inhibiting ovulation (Ljundquist et al;, 1988) and single doses have profound, long lasting inhibitory effects on serum LH concentrations in castrate female cynamologous monkeys (Leal et al, 1988). It has also been shown to be capable of inducing long term chemical castration in intact adult male rats and cynamologous monkeys, and to have an inhibitory effect on tumour growth in the Dunning R3327 prostatic carcinoma model, similar to that of castration (Habenicht et al, 1990). The new antagonist should therefore be of substantial clinical interest in all those conditions in which medical castration is desirable, particularly in the management of prostatic cancer and in various gynaecological disorders (McLachlan et al., 1986). Current administration is limited to the parenteral route. However the dose of analogue that can be delivered by this route is limited due to the poor solubility of the antagonist. Thus clinical trials of the long term effect of ANTIDE have been reduced to doses of 2.5 mg or lower.

The oral route of administration of peptides such as LHRH and its analogues as pharmaceuticals in the treatment of systemic conditions has met with little success. In general the amount of peptide required for successful oral administration has been 100 to 1000 times the dose required for parenteral deliver, thus making the administration of these agents via this route prohibitively expensive. There are two fundamental reasons for the lack of success. Firstly, the intestinal milieu has a high degree of proteolytic activity, which rapidly degrades most peptides. Secondly, while there are well defined uptake mechanisms for individual amino acids and di-peptides, there is no general mechanism for polypeptides to be transported across the membrane of the mucosal epithelium into the circulation. Rather, this membrane is designed as a general barrier prohibiting the uptake of the numerous foreign proteins encountered in this environment. Thus, although a peptide may be modified to withstand the enzymatic barrage encountered in the intestine, such modification is of little value if the peptide cannot subsequently cross the mucosal barrier and enter the systemic circulation.

Recent work by the current inventor (PCT/AU86/00299) has however provided a method to overcome the mucosal barrier. This method takes advantage of the natural intrinsic factor (IF) mediated uptake mechanism for vitamin B12 (VB12). VB12 is a naturally occurring dietary molecule which is actively taken up from the intestine. During this process it first binds to IF in the upper small intestine. The VB12-IF complex then passes down the small intestine and binds to an IF receptor located on the surface of the ileal epithelium. The whole [VB12-IF-Receptor] complex is then internalized by receptor-mediated endocytosis and some time later the VB12 appears in serum.

PCT application PCT/AU86/00299 (WO87/02251) describes methods to modify chemically VB12 to provide suitable functional groups for conjugation of the VB12 to various drugs and peptide/protein pharmaceuticals. When the [VB12-pharmaceutical] complex is administered orally it is possible to utilise the natural IF-mediated VB12-uptake system to deliver the pharmaceutical to the circulation.

As the oral route of administration is the most preferable means of delivering a pharmaceutically active agent, there is a large and valuable market for any process which permits the oral delivery of LHRH antagonists to humans. Such a process would be available by the formation of a complex between VB12 or analogues thereof and LHRH antagonists.

SUMMARY OF THE INVENTION

In a first aspect the present invention consists in analogues of ANTIDE.

ANTIDE is a particularly suitable molecule for oral administration, as it contains very few natural amino acids and as such is highly resistant to the action of pepsin, trypsin or chymotrypsin. However, ANTIDE itself needs to be modified slightly to provide a suitable site for conjugation to VB12. The inventor has found that it is possible to synthesize three analogues of ANTIDE which are suitable for conjugation to VB12, namely N-Ac-D-Nal(2), D-Phe (pCl), D-Pal(3), Ser, Lys (Nic), D-Lys, Leu, Lys(iPr), Pro, D-Ala-NH$_2$ (D-Lys$_6$ANTIDE or ANTIDE-1), N-Ac-D-Nal(2), D-Phe (pCl), D-Pal(3), Ser, Lys , D-Lys(Nic), Leu, Lys(iPr), Pro, D-Ala-NH$_2$ (Lys$_5$ ANTIDE or ANTIDE-2) and N-Ac-D-Nal(2), D-Phe (pCl), D-Pal(3), Ser, Lys (Nic), D-Lys (Nic), Leu, Lys, Pro, D-Ala-NH$_2$ (Lys$_8$ANTIDE or ANTIDE-3).

A second aspect of the present invention provides a complex between the VB12 or an analogue of VB12 and the LHRH antagonists of the first aspect, wherein the ability of VB12 or an analogue of VB12 to undergo the binding reactions necessary for the uptake and transport of VB12 in a vertebrate host and the activity of the LHRH antagonist are substantially maintained.

The VB12 analogues include any variation or derivative of VB12 which posses binding activity to intrinsic factor. Preferred analogues of VB12 include cyanocobalamin (CN-Cbl), aquocobalamin, adenosylcobalamin, methylcobalamin, hydroxycobalamin, cyanocobalamin carbanalide, 5-methoxybenzylcobalamin [(5-MeOBz)CN-Cbl], as well as the desdimethyl, monoethylamide and methylamide analogues of all of the above. Other analogues include coenzyme B12, 5'-deoxyadenosylcobalamin, chlorocobalamin, sulfitocobalamin, nitrocobalamin, thiocyanatocobalamin, benzimidazole derivatives such as 5,6-dichlorobenzimadazole, 5-hydroxybenzimidazole, trimethylbenzimidazole, as well as adenosylcyanocobalamin [(Ade)CN-Cbl], cobalamin lactone, cobalamin lactam, and the anilide, ethylamide, monocarboxylic and dicarboxylic acid derivatives of VB12 or its analogues.

Preferred derivatives of VB12 also include the mono-, di- and tricarboxylic acid derivatives of propionamide derivatives of VB12. Other derivatives include analogues of VB12 in which the cobalt is replaced by zinc or nickel. The corrin ring of VB12 or its analogues may also be substituted with any substituent which does not effect its binding to IF, and such derivatives of VB12 or its analogues are part of this invention. Other derivatives and analogues of VB12 are discussed in Schneider, Z and Stroinski, A.: (Walter De Gruyter, Berlin, N.Y.; 1987), the disclosure of which is incorporated herein by reference.

Suitable extended spacers for the conjugation include disuccinimidyl suberate (DSS), bis(sulfosuccinimidyl) suberate (BSS), ethylene glycolbis(succinimidylsuccinate) (EGS), ethylene glycolbis(sulfosuccinimidylsuccinate) (Sulfo-EGS), p-aminophenylacetic acid, dithiobis (succinimidylpropionate) (DSP), 3,3'-dithiobis (sulfosuccinimidylpropionate) (DTSSP), disuccinimidyl tartarate (DST), disulfosuccinimidyl tartarate (Sulfo-DST), bis [2-(succinimidooxycarbonyloxy)-ethylene]sulfone (BSOCOES), bis [2-(sulfosuccinimidooxycarbonyloxy)-ethylene]sulfone (Sulfo-BSOCOES), dimethyl adipimidate.2 HCl (DMA), dimethyl pimelimidate.2HCl (DMP), dimethyl suberimidate.2HCl (DMS).

Suitable cross-linking agents for use in the preparation of thiol-cleavable biodegradable linkers include N-succinimidyl 3-(2-pyridyldithio)propionate (SPDP), iminothiolane, sulfosuccinimidyl 6-[3-(2-pyridyldithio) propionamido] hexanoate (Sulfo-LC-SPDP), succinimidyl 6-[3-(2-pyridyldithio) propionamido] hexanoate (LC-SPDP), sulfosuccinimidyl 6-[α-methyl-α-(2-pyridyldithio) toluamido]hexanoate (Sulfo-LC-SMPT), 1,4-di[3'-(2'-pyridyldithio)propionamido]butane (DPDPB), 4-succinimidyloxycarbonyl-α-methyl-α-(2-pyridyldithio)-toluene (SMPT), dimethyl 3,3'dithiobispropionimidate.2 HCl (DTBP).

In a further aspect the invention provides a method for preparing biodegradable complexes between VB12 and LHRH antagonists such as the ANTIDE analogues of the first aspect, such that the VB12 is cleaved from the LHRH antagonist in vivo.

In yet another aspect the invention provides a complex comprising an ANTIDE analogue of the first aspect bound to VB12 carrier or an analogue thereof where more than one ANTIDE analogue is bound to the carrier.

In yet another aspect the invention provides a method for the oral delivery of LHRH antagonists whereby the LHRH antagonist will be transepithelially transported from the intestine to the circulation of the vertebrate host.

In another aspect, the invention describes a new class of ANTIDE analogues which possess greater solubility in physiological solvents. These analogues can be administered systemically.

BRIEF DESCRIPTION OF THE DRAWINGS

In order that the nature of the present invention may be more clearly understood, preferred forms thereof will now be described with reference to the following examples and figures in which:

FIG. 1 is a graph showing the median inhibitory concentrations (IC50), determined by in vitro bioassay, for blockade of LHRH-stimulated release of LH from rat pituitary cells by ANTIDE, its analogues and VB12-conjugates. Median inhibitory concentrations of ANTIDE, ANTIDE analogues and VB12-ANTIDE conjugates for antagonising LHRH-stimulated release of LH from rat anterior pituitary cell cultures during 4 hours. Results for conjugates are given as ng of the incorporated analogue/ml (final concentration in culture well). Results that do not differ from each other (i.e. $P>0.05$) are grouped under a common letter.

FIG. 2 is a graph showing in vitro bioassay for blockade of LHRH-stimulated release of LH from rat pituitary cells by ANTIDE, ANTIDE-3 its VB12-conjugates Assay conditions are similar as those given in FIG. 1.

FIG. 3 is a graph showing reduction in serum LH level in castrate rats following injection of ANTIDE, ANTIDE-1 or ANTIDE-1-VB12-conjugates. The in vivo effect of subcutaneous injection of ANTIDE or VB12-ANTIDE conjugates was examined in 6 week old castrate rats. Twenty-four hours after subcutaneous injection of a 100 μg dose of the various ANTIDE analogues, the rats were killed and trunk blood collected for analysis of serum LH levels by RIA (see Puénte & Catt, 1986).

FIG. 4 is a graph showing reduction in serum LH levels in castrate rats following subcutaneous injection of 100 μg doses of ANTIDE, ANTIDE-3 or ANTIDE-3-VB12-conjugates.

MATERIALS

Pituitary Cell Assay for LH Release

Cell cultures were prepared from the anterior pituitaries of 4 month old Sprague-Dawley rats. Cells were dispersed as a single cell suspension of 250,000 viable cells per ml in Dulbecco's modified Eagle's Medium with 10% foetal bovine serum plus antibiotics. Aliquots of 0.5 ml were dispensed into multi well tissue culture plates and maintained at 30° C. in an enclosed humidified atmosphere of 5%

$CO_2$ in air. Cells were cultured for 5 days and medium removed. The medium was replaced with fresh medium containing a range of doses of ANTIDE, ANTIDE analogues or VB12-ANTIDE conjugates. After 4 hours 10 nM LHRH was added to each well. Cells were incubated for a further 4 hours afterewhich medium was removed for the determination of the amount of FSH and LH released into the medium by radio-immuno assay (RIA).

Castrate Rat Model

Adult Sprague Dawley rats were castrated and maintained in the animal house for one week prior to administration of test substances. ANTIDE or analogues were tested by subcutaneous injection into the castrate rats. Groups of 5 rats were used as controls and for collection of blood samples from the external jugular vein at 24 hours post-dose. LH was measured by a standard radio-immunoassay.

IF Assay

The affinity of the various VB12-ANTIDE conjugates for IF was determined in a competitive binding assay (Russell-Jones, 1994). Dilutions of unlabelled VB12 or VB12 analogue or conjugate were mixed with 1 ng $^{57}$CoVB12 (Amersham). One IU of IF (a unit of IF is the quantity of IF required to bind 1 ng of VB12) was then added to the mixture, and the mixture was incubated for 20 min at room temperature (RT) before the addition of a solution of 5% activated charcoal in 0.1% BSA (IF and VB12-free, Sigma). Samples were centrifuged and the counts in the supernatant (IF bound) and pellet (free $^{57}$CoVB12) were used to determine the relative affinity of IF for the material tested.

Synthesis of ANTIDE Analogues

Three ANTIDE analogues containing single, unmodified lysines, namely D-Lys$^6$ANTIDE or ANTIDE-1; Lys$^5$ANTIDE or ANTIDE-2 and Lys$^8$ANTIDE or ANTIDE-3 (see Table 1.) were synthesized on an Applied Biosystems Peptide Synthesizer. Peptides were cleaved from the resin and purified by Reverse Phase HPLC, using a gradient of 5–100% acetonitrile in 0.1% TFA.

TABLE 1

Sequence of ANTIDE and its analogues.

| Analogue | Sequence |
| --- | --- |
| ANTIDE | N-Ac-D-Nal(2), D-Phe (pCl), D-Pal(3), Ser, Lys (Nic), D-Lys(Nic), Leu, Lys(iPr), Pro, D-Ala-NH$_2$ |
| D-Lys$^6$ANTIDE or ANTIDE-1 | N-Ac-D-Nal(2), D-Phe (pCl), D-Pal(3), Ser, Lys (Nic), D-Lys, Leu, Lys(iPr), Pro, D-Ala-NH$_2$ |
| Lys$^5$ANTIDE or ANTIDE-2 | N-Ac-D-Nal(2), D-Phe (pCl), D-Pal(3), Ser, Lys , D-Lys(Nic), Leu, Lys(iPr), Pro, D-Ala-NH$_2$ |
| Lys$^8$ANTIDE or ANTIDE-3 | N-Ac-D-Nal(2), D-Phe (pCl), D-Pal(3), Ser, Lys (Nic), D-Lys(Nic), Leu, Lys, Pro, D-Ala-NH$_2$ |

Two of the analogues, ANTIDE-1 and ANTIDE-3, have considerable potency in vitro and ANTIDE-3 has activity comparable to the native ANTIDE in vivo. The direct covalent conjugation of the "e" isomer carboxylate of VB12 (eVB12) to either ANTIDE-1, ANTIDE-2 or ANTIDE-3 was found to reduce the bioactivity of the ANTIDE analogue to levels substantially lower than ANTIDE itself regardless of whether the analogue was tested in vitro or in vivo.

Direct Conjugation of ANTIDE Analogues to Monocarboxy-VB12

In order to obtain a functional group suitable for conjugation of the VB12 to ANTIDE, cyanocobalamin (VB12) was first hydrolysed in 0.4M HCl for 72 hours. The e isomer of monocarboxy vitamin B12 (eVB12, e isomer), which has previously been shown to have the highest affinity for IF of the three isomers, was separated from the b and d isomers (also formed during acid hydrolysis of cyanocobalamin) by a combination of Dowex 1X2 chromatography, and semi-preparative C-18 RP-HPLC developed with a gradient of 5–100% acetonitrile in 0.1% TFA.

Aminoethyl-eVB12 was prepared by reacting the eVB12 isomer with 1,2-diaminoethane at pH 6.5 using a twenty-fold molar excess of the diamine over e isomer and a twenty fold molar excess of 1-ethyl-3-(3-dimethyl-aminopropyl) carbodiimide (EDAC; Biorad, Richmond, Calif.). The aminoethyl derivative was purified by RP-HPLC on a semi-preparative C-4 column using a 5–100% acetonitrile gradient in 0.1% TFA. Eluted material was further purified by S-Sepharose chromatography. The amino derivative was eluted with 0.1M HCl, followed by extraction into phenol, and back-extraction into water after the addition of dichloromethane to the phenol phase. Aminoethyl-eVB12 was then recovered from the water phase by lyophilization.

The three ANTIDE analogues were conjugated to eVB12 using the carbodiimide, EDAC, and the products (B12-ANT1, B12-ANT2 and B12-ANT3; depending on whether the complex was formed between ANTIDE-1, ANTIDE-2 or ANTIDE-3, respectively) were purified by chromatography on Sephadex G-25 in 10% acetic acid prior to RP-HPLC on a semi-preparative C-4 column, as described above.

Conjugation of VB12 to ANTIDE using Cross-Linker Containing a Hindered Thiol Aminoethyl-eVB12 was reacted with 4-succinimidyloxycarbonyl-α-methyl-α-(2-pyridyldithio) toluene (SMPT; Pierce). Iminothiolated ANTIDE-1 and ANTIDE-3 were prepared as outlined above. The SMPT-derivative of aminoethyl-eVB12 was then reacted with the thiolated ANTIDE-1 and -3 derivatives as described above, followed by subsequent purification of B12-TSS-ANT1 and B12-TSS-ANT3 by the usual method (Table 2).

Formation of a Non-Cleavable Thio-Ether Linkage Between VB12 and ANTIDE 6-(Iodoacetamido)hexylamido-eVB12 in diisopropyl-ethyl amide/dimethyl formamide (DMF/DIEA; 1:20 v/v) was deoxygenated with argon for ten minutes, and a solution of iminothiolated ANTIDE-1 or -3 in DMF was then added dropwise to the stirred solution. Each reaction mixture was stirred for 30 minutes at room temperature then diluted with water, filtered and the products, B12-SC-ANT1 and B12-SC-ANT-3, were purified by preparative RP-HPLC (Table 2).

TABLE 2

Structure of spacer and IF affinity of $VB_{12}$-Antide conjugates
General Structure: $eVB_{12}$-SPACER-Antide

| Conjugate Name | Antide analogue | SPACER | IF affinity |
|---|---|---|---|
| direct | Antide 1<br>Antide 3 | None | N/T<br>N/T |
| anilido | Antide 1<br>Antide 3 | —C(O)—NH—C6H4—CH2CONH— | 53%<br>36% |
| EGS-derived | Antide 1<br>Antide 3 | Ac-NH-CH2CH2-NH-C(O)-CH2CH2-C(O)-O-CH2CH2-O-C(O)-CH2CH2-C(O)-N— | 30%<br>N/T |
| DSS-derived | Antide 3 | Ac-NH-CH2CH2-NH-C(O)-(CH2)4-C(O)-N— | N/T |
| dithio-propionyl | Antide 1 | Ac-NH-CH2CH2-NH-C(O)-CH2-S-S-CH2CH2-C(O)-N— | 65% |
| dithio-imino | Antide 3 | Ac-NH-CH2CH2-NH-C(O)-CH2-S-S-CH2CH2CH2-C(=NH2+)-NH— | N/T |
| hexylthio-imino | Antide 1<br>Antide 3 | Ac-NH-(CH2)6-NH-C(O)-CH2-S-CH2CH2CH2-C(=NH2+)-NH— | 82%<br>65% |
| hexyltoluyl-dithio imino | Antide 1<br>Antide 3 | Ac-NH-(CH2)6-NH-C(O)-C6H4-CH(CH3)-S-S-CH2CH2CH2-C(=NH2+)-NH— | 54%<br>37% |
| GGEA | Antide 1<br>Antide 3 | Ac-NH-CH2-C(O)-NH-CH2-C(O)-NH-CH(C(O)NH-)-CH2CH2-C(O)-NH-CH(CO2Me)-CH3 | 60%<br>48% |

N.T. Not tested

Conjugation of VB12 to ANTIDE Using a Transglutaminase Cleavable Linkage

ANTIDE-1 and -3 were taken up in 5% DIEA/DMF and the N-succinimidyl ester derivative of eVB12-GGEA-OMe (eVB12-GlyGlyGluAla) in DMF (100 µl) was added. Each reaction mixture was stirred for 30 minutes at room temperature, then diluted with 2% acetic acid, and filtered. The products, B12-TP-ANT1 and B12-TP-ANT3 were purified by RP-HPLC, lyophilized and stored under dessicant before use (Table 2).

Statistical Analysis

Data from replicate individuals (in vivo trials), and from replicate experiments (in vitro trials) were subjected to one-way analysis of variance, and Tukey HSD post hoc tests were applied for the pairwise comparison of means, which were deemed to be significantly different at a probability level of $P<0.05$.

Affinity of VB12-ANTIDE Conjugates for Intrinsic Factor

All VB12-ANTIDE conjugates tested showed good affinity for Intrinsic Factor (Table 2). In fact, most conjugates had a relative affinity which was higher than that of the eVB12 isomer used to make the conjugate (normally around 35%).

EXAMPLE 1

Formation of VB12-ANTIDE Analogue Conjugates Using Non-Cleavable Homobi-Functional Cross-Linkers The direct conjugation between VB12 and ANTIDE-1 and ANTIDE-3 produced conjugates with greatly reduced bioactivity when compared to ANTIDE. The close proximity of VB12 to ANTIDE using this conjugation strategy would sterically interfere with the binding of ANTIDE to the LHRH receptor. In order to reduce the steric effect possibly seen with direct conjugation, non-cleavable linkers were used to produce covalent complexes between aminoethyl "e"VB12 and ANTIDE-1 and 3. Briefly, the ANTIDE-1 and 3 were reacted with a 1.5 molar excess of either Disuccinimidyl suberate (DSS) or Ethylene glycolbis (succinimidylsuccinate) (EGS) for 10 minutes at Room Temperate (RT). Aminoethyl"e"VB12 was then added and the reaction allowed to proceed overnight. Conjugated material was purified by chromatography on Sephadex G-25 in 10% acetic acid, followed by Reversed Phase HPLC (RP-HPLC). The VB12-Anilido-ANTIDE-1 and ANTIDE-3 conjugates were formed by reaction of aminoethyl"e"VB12 with p-aminophenylacetic acid using EDAC/NHS. The VB12-anilide, was in turn conjugated to ANTIDE-1 and ANTIDE-3 using EDAC/NHS. The conjugated material was purified by G-25 chromatography in 10% acetic acid followed by RP-HPLC.

EXAMPLE 2

Formation of VB12-ANTIDE Analogue Conjugates Using Spacers

Figure 1:
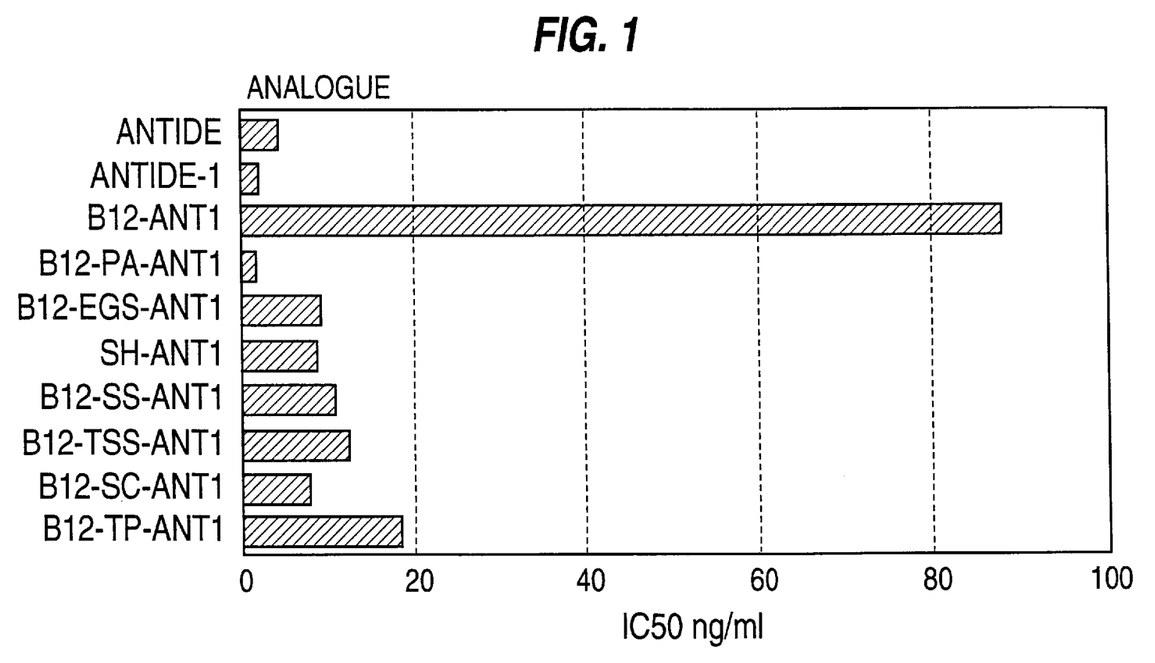
Figure 2:
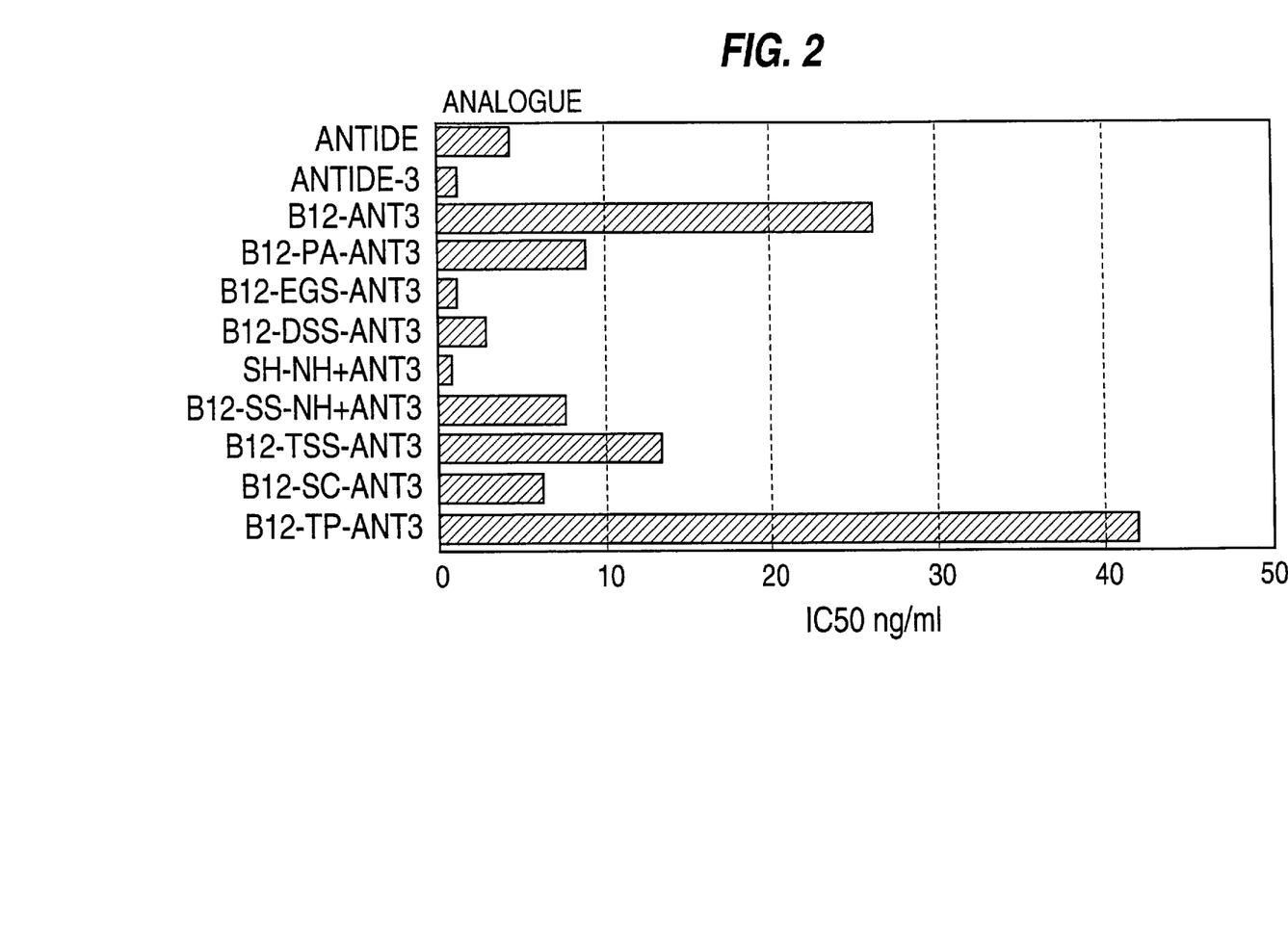
Figure 3:
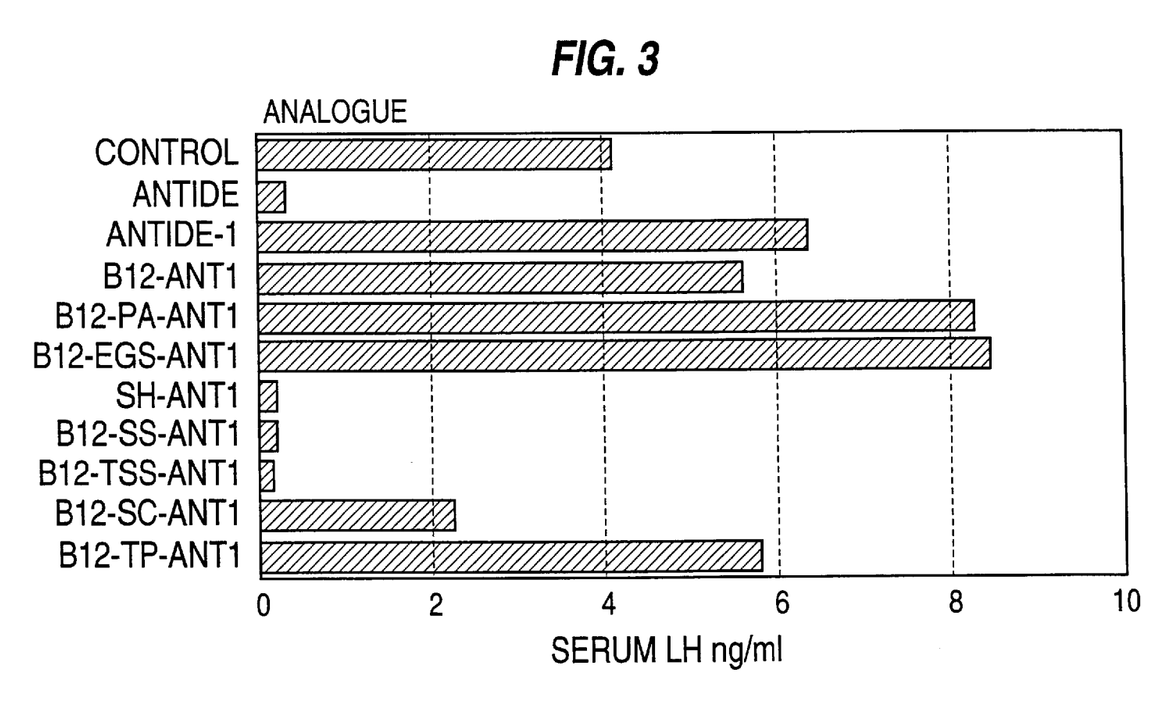
Figure 4:
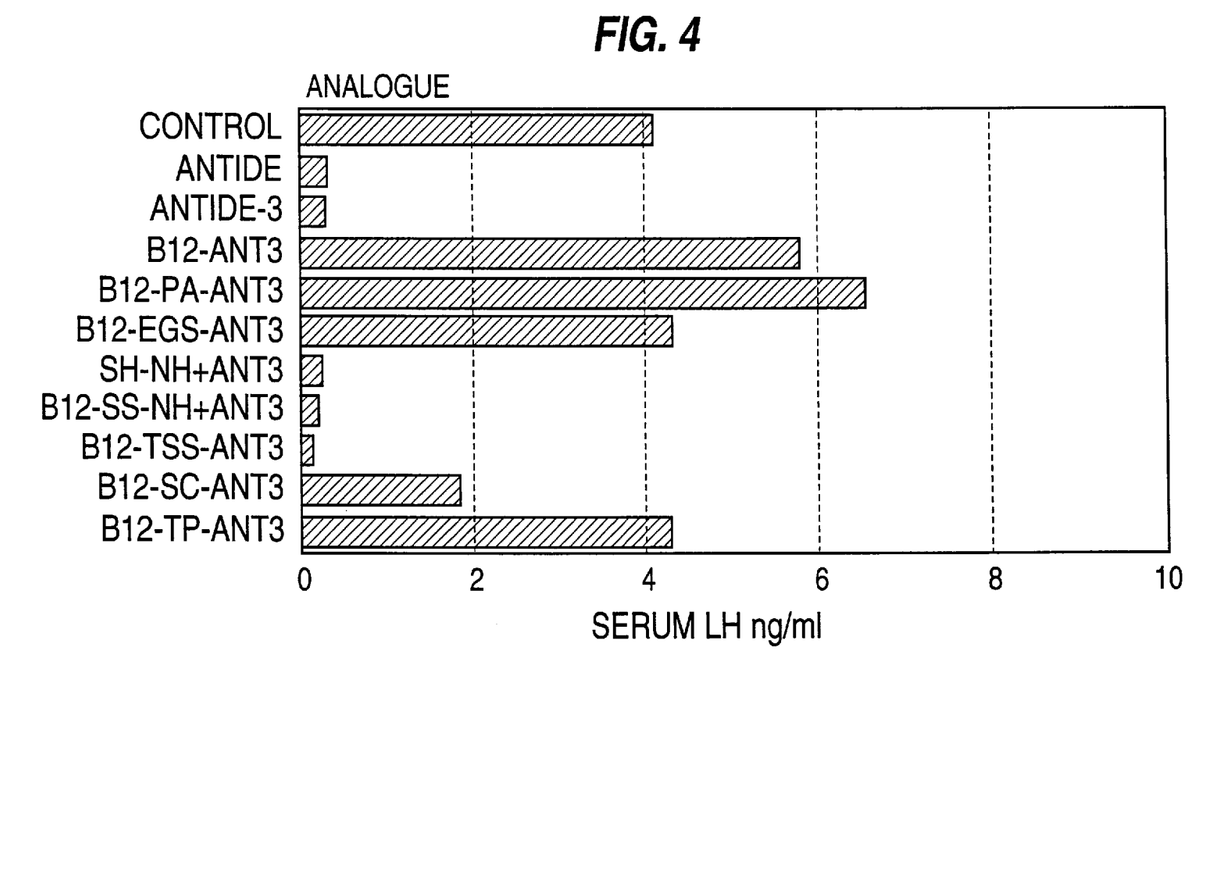

Preparation of conjugates between $VB_{12}$ and ANTIDE-1 and ANTIDE-3 with either hydrophilic spacers such as EGS (16.1 Å), hydrophobic spacers such as DSS (11.4 Å), or a shorter bulky anilido group, greatly increased the in vitro bio-activity of the conjugates, to levels comparable to that of the parent analogue (FIGS. 1 & 2). Thus, B12-PA-ANT1, B12-EGS-ANT3 and B12-DSS-ANT3 all had bioactivities comparable to that of native ANTIDE (FIGS. 1 & 2). By contrast, the in vivo bioactivity of these conjugates when given sc to rats was very low, as evidenced by the failure of these conjugates to cause a significant drop in serum LH levels in castrate rats, even at doses of 100 ug of analogue. ANTIDE and ANTIDE-3, on the other hand, were active at doses as low as 12.5 ug (FIGS. 3 & 4). It thus appeared that some factor other than steric hindrance was affecting the in vivo activity of these VB12-ANTIDE conjugates (cf. FIGS. 1 with 3 and 2 with 4).

EXAMPLE 3

Formation of VB12-ANTIDE Conjugates Using Thiol-Cleavable Cross-Linkers

Linkage of VB12 to ANTIDE analogues using extended hydrophilic or hydrophobic spacers produced conjugates which had similar in vitro activity to native ANTIDE. Parenteral administration of these conjugates, however, had little effect in lowering serum LH levels of castrate rats over the range of doses tested. These results suggested that although the general strategy of increasing the bioactivity of the VB12-ANTIDE conjugates by the introduction of extended spacers was correct, the conjugate so formed had reduced activity in vivo, possibly due to the presence of the VB12 molecule in the conjugate. Conjugates were therefore prepared in which the covalent linker contained a biodegradable disulfide bond, which would be reduced in vivo, presumably by glutathione in serum. Briefly, aminoethyl-"e"VB12 was reacted with N-succinimidyl 3-(2-pyridyldithio)propionate (SPDP). The dithiopyridyl-aminoethyl"e"VB12 (DTP"e"VB12) product was purified by RP-HPLC. A free thiol was introduced onto ANTIDE-1 by reaction with SPDP. The dithiopyridyl group was then reduced with mercapto-ethanol and the product purified by RP-HPLC. Similarly, a free thiol was introduced into ANTIDE-3 by reaction with iminothiolane. The thiolated product (SH-HN$^+$ANTIDE-3) was purified by RP-HPLC. Formation of the disulfide linked VB12-ANTIDE-1 and VB12-ANTIDE-2 conjugates was achieved by reaction of the thiolated ANTIDE derivative with DTP"e"VB12 in 2.5% acetic acid for 24 hours. The conjugated material was purified by Sephadex G-25 chromatography, followed by RP-HPLC.

EXAMPLE 4

Formation of VB12-ANTIDE Analogue Conjugates Using Biodegradable Linkers

In order to reduce the possibility of removal of the VB12-ANTIDE conjugates from the circulation following injection, VB12-ANTIDE conjugates were prepared using a thiol-cleavable, disulfide-containing, spacer. This spacer would potentially allow the cleavage of ANTIDE from VB12 by the low levels of reduced glutathione in serum. Conjugates were therefore prepared between ANTIDE-1 and ANTIDE-3 using a thiol-cleavable spacer (SS) and a hindered thiol group (TSS). The presence of the hindered thiol in the latter spacer should mean that is would be cleaved more slowly upon exposure to serum glutathione. A conjugate containing a non-cleavable thioether linker of similar length (SC) was prepared.

The thiol-cleavable B12-SS-ANT1 and B12-SS-NH$^+$ANT3 conjugates were found to have similar in vitro bioactivity to the extended spacer conjugates described above (FIGS. 1 & 2, Tables 5 & 6). Administration of B12-SS-NH$^+$ANT3 parenterally to castrate rats resulted in a similar reduction in serum LH to that seen with the unmodified ANTIDE-3, while B12-SS-ANT1 had a similar bioactivity in vivo to native ANTIDE (Table 6). Thus, the use of the thiol-cleavable spacer, rather than a non-cleavable spacer, in the preparation of the VB12-ANTIDE conjugates, while having little effect on the IC50 of the VB12-spacer-ANTIDE conjugates in the in vitro assay, greatly increased the potency of these conjugates in vivo, to levels similar to ANTIDE (FIGS. 3 & 4, Tables 5 & 6). The incorporation of a tolyl-group, or hindered thiol, did not significantly change the in vitro or in vivo activity of either analogue relative to the respective unhindered thiol analogue. The non-cleavable conjugates formed with the thio-ether linkage were found to have similar activity to the thiol analogue when tested in vitro, however, this analogue had a greatly reduced activity when tested in vivo.

TABLE 3

In vitro bioassay for blockade of LHRH-stimulated release of LH from rat pituitary cells by ANTIDE, its analogues and $VB_{12}$-conjugates

| Analogue | IC50 | [n] |
|---|---|---|
| ANTIDE | 4.4 ± 0.7$^a$ | [20] |
| ANTIDE-1 | 2.1 ± 0.3$^a$ | [8] |
| ANTIDE-2 | 11.7 ± 2.7$^{a,b}$ | [5] |
| ANTIDE-3 | 1.2 ± 0.2$^a$ | [13] |
| B12-ANT1 | 88 ± 21$^c$ | [5] |
| B12-ANT2 | 105 ± 21$^c$ | [4] |
| B12-ANT3 | 36 ± 10 | [4] |

Median inhibitory concentrations (IC50) of ANTIDE, ANTIDE analogues and VB 12-ANTIDE conjugates for antagonising LHRH-stimulated release of LH from rat anterior pituitary cell cultures during 4 hours. Results for conjugates (mean +/– S.E.) are given as ng of the incorporated Antide analogue/ml (final concentration in culture well) from n independent trials. Results that are not significantly different from each other (i.e. P > 0.05) are grouped under a common subscript letter.

TABLE 4

Serum LH levels in castrate rats following subcutaneous injection of ANTIDE, ANTIDE analogues or their VB$_{12}$-conjugates

| Analogue | Dose (ug) | Mean LH ± s.d. (ng/ml) |
|---|---|---|
| Expt. 1 | | |
| Control | | 7.35 ± 1.90[a]* |
| ANTIDE | 100 | 0.29 ± 0.06[b] |
|  | 50 | 0.24 ± 0.06[b] |
| ANTIDE-1 | 100 | 6.37 ± 1.00[a] |
| ANTIDE-2 | 100 | 9.51 ± 3.11[a] |
| ANTIDE-3 | 100 | 0.27 ± 0.05[b] |
| B12-ANT3 | 50 | 10.11[a] |
| Expt. 2 | | |
| Control | | 6.69[a] |
| ANTIDE | 50 | 0.44 ± 0.02[b] |
| ANTIDE-3 | 16.7 | 0.71 ± 0.2[b] |
| B12-ANT1 | 50 | 5.44 ± 1.4[a] |
| B12-ANT2 | 50 | 5.56 ± 0.97[a] |
| B12-ANT3 | 50 | 5.51 ± 0.22[a] |

*A common letter signifies that the mean values do not significantly differ from one another ($P > 0.05$)

TABLE 5

In vitro bioassay for blockade of LHRH-stimulated release of LH from rat pituitary cells by ANTIDE, its analogues and disulfide linked VB$_{12}$-conjugates.

| Analogue | IC50* | [n] |
|---|---|---|
| ANTIDE | 4.4 ± 0.7[a] | [20] |
| ANTIDE-1 | 2.1 ± 0.3[a] | [8] |
| B12-SS-ANT1 | 10.4 ± 4.0[b] | [3] |
| ANTIDE-3 | 1.2 ± 0.2[c] | [15] |
| HS-NH⁺ANT3 | 0.72 ± 0.11[a,c] | [3] |
| B12-SS-NH⁺ANT3 | 7.4 ± 0.8[a,b] | [3] |

*(See legend to Table 3 for further details).

TABLE 6

Reduction in serum LH level in castrate rats following subcutaneous injection of ANTIDE, ANTIDE analogues, or their disulfide linked VB$_{12}$-conjugates

| Analogue | Dose (ug) of Analogue | Serum LH, % of matching control* (mean ± s.d.) |
|---|---|---|
| ANTIDE | 25.0 | 4 ± 0.70 [#1] |
|  | 12.5 | 15.3 ± 5.40 [#3] |
|  | 6.3 | 80.6 ± 43.8 [#3] |
|  | 3.1 | 100.2 ± 36.8 [#3] |
| ANTIDE-1 | 100 | 87.6 ± 13.6 [#1] |
| B12-SS-ANT1 | 25.0 | 19.8 ± 4.80 [#5] |
|  | 12.5 | 34.4 ± 14.7 [#5] |
|  | 6.3 | 73.9 ± 25.4 [#6] |
| ANTIDE-3 | 100.0 | 3.7 ± 0.70 [#1] |
|  | 25 | 18.0 ± 5.50 [#5] |
|  | 12.5 | 43.0 ± 12.8 [#3] |
|  | 6.3 | 116.1 ± 42.4 [#3] |
| HS-NH⁺ANT3 | 50.0 | 28.2 ± 11.4 [#5] |
|  | 25.0 | 77.3 ± 17.2 [#5] |
|  | 12.5 | 112.8 ± 20.9 [#5] |
| B12-SS-NH⁺ANT3 | 50.0 | 16.5 ± 5.10 [#5] |
|  | 25.0 | 23.8 ± 9.20 [#5] |
|  | 12.5 | 63.8 ± 16.5 [#6] |
|  | 6.3 | 78.8 ± 24.4 [#6] |

EXAMPLE 5

Formation of VB12-ANTIDE Analogue Conjugates Using a Transglutaminase Cleavable Linker Conjugates formed between VB12 and ANTIDE-1 and ANTIDE-3 using a transglutaminase cleavable γ-glutamyl-ε-lysine bond, (B12-TP-ANT1 and B12-TP-ANT3) were found to have poor activity in vitro, and negligible activity in vivo at the doses tested, suggesting that this bond was not cleaved in vitro or in vivo. The stereo-specificity may have inhibited the cleavage of the ANTIDE-1 conjugates (due to the presence of the D-lysine group), while steric hindrance may have prevented the transglutaminase enzyme from cleaving both the ANTIDE-1 and ANTIDE-3 conjugates.

EXAMPLE 6

Formation of VB12-ANTIDE-Analogue Lysyl-Polyglutamate Conjugates Using Thiol-Cleavable Cross-Linkers It is desirable to increase the amount of drug, or its analogues, which can be taken up by the VB12-transport system, by the linkage of multiple copies of the drug to a polymeric backbone, to which is conjugated one or more VB12 molecules. A process is described for the formation of such a VB12-drug-polymer complexes.

a) Formation of DTP-Lysyl-Polyglutamate

Poly-glutamate (100 mg) (MW 64,600–70,000; Sigma), was reacted with EDAC (100 mg) and NHS (50 mg in acetone) for 10 minutes at RT. Lysine (400 mg in 4 ml 1% NaHCO$_3$) was added and allowed to react overnight (O/N). The product, Lysyl-Polyglutamate (LPG), was purified by extensive dialysis against DW, and then lyophilized.

The dithiopyridyl derivative of LPT, was obtained by reacting Dithiopyridyl-propionic acid (50 mg) with O-(N-Succinimidyl)-N,N,N'N'-tetramethyluronium tetrafluoroborate (TSTU) (100 mg) and N-Ethyldiisopropyl amine (100 mg; DIEA) in DMF for 1 hour. The succinimidyl ester so formed was added directly to 100 mg LPG dissolved in 4 ml 2% NaHCO$_3$. The reaction was allowed to proceed O/N after which the product (DTP-LPG) was purified by exhaustive dialysis against DW, and then lyophilized.

b) Preparation of Iminothiolated ANTIDE-1

ANTIDE-1 (20 mg) was dissolved in 300 μl 5% DIEA in DMF containing 5 mg EDTA plus 5 mg DTT, which had been degassed under argon. Iminothiolane (20 mg in 50 μl DIEA/DMF plus 50 μl Borate buffer, 100 mM pH 8.2) was added and reacted for 60 minutes before purification by RP-HPLC and lyophilization.

c) Preparation of Iminothiolated Aminoethyl-VB$_{12}$

Aminoethyl"e"VB12 (20 mg) was dissolved in 300 μl 5% DIEA in DMF containing 5 mg EDTA plus 5 mg DTT, which had been degassed under argon. Iminothiolane (20 mg in 50 μl DIEA/DMF plus 50 μl Borate buffer, 100 mM pH 8.2) was added and reacted for 60 minutes before purification by RP-HPLC and lyophilization.

d) Formation of VB12-ANTIDE-Lysyl-Polyglutamate

DTP-LPG was dissolved at 20 mg/ml in DW. Iminothiolated-aminoethyl-VB12 was dissolved at 5 mg/ml in DW and added to the DTP-:PG (1:20 w/w) and allowed to react for 20 min at RT before the addition of iminothiolated-ANTIDE-1 (50 mg/ml in DW) dropwise with stirring. The reaction mixture was kept at pH 6.5–7.0 by the addition of Tris.HCL pH 7.0 and NaAcetate, pH 5.5. The reaction proceeded overnight after which the product was purified by dialysis and then lyophilized. The composition of the product was determined by amino acid analysis and found to contain 1:5:21,ANTIDE-1:Lysine:Glutamate, or roughly 25% by weight ANTIDE.

The development of an LHRH antagonist suitable for use in humans for the treatment of hormone dependent mammary and prostate cancer has in the past been limited by the low potency of these molecules, their poor solubility in physiological buffers, and their poor oral bioavailability. In an attempt to resolve these problems, the present inventor has examined the possibility of combining the relatively high bioactivity of the potent LHRH antagonist, ANTIDE, with the high oral bioavailability of vitamin B12. ANTIDE is particularly suitable for oral delivery, since it is composed of many unnatural amino acids, and is resistant to the action of trypsin or chymotrypsin. ANTIDE, however, must be modified in such a way as to provide a suitable site for conjugation to VB12, as well as retaining full biological potency. ANTIDE normally possesses modified lysine residues at positions 5, 6 and 8 viz:- Lys(Nic), D-Lys(Nic) and Lys(iPr), respectively. The removal of these modifications at either of the three sites provides a free amine suitable for conjugation to VB12. Two derivatives of ANTIDE, D-Lys$^6$-ANTIDE (ANTIDE-1) and Lys$^8$-ANTIDE (ANTIDE-3) suitable for conjugation to VB12 were synthesized, and found to have high potency in the in vitro pituitary cell assay. ANTIDE-3 was also found to be highly potent when administered s.c. to rats, although ANTIDE-1, was found to have negligible antagonist activity, possibly due to an alteration in the rate of its clearance from serum. The in vitro and in vivo potency of either analogue was, however, greatly reduced by direct conjugation to VB12 (Tables 3 & 4), presumably due to steric interference with binding of the conjugate to the pituitary receptor for LHRH by the bulky VB12 molecule in close proximity to ANTIDE.

In order to reduce the steric effect seen with direct conjugation of VB12 to ANTIDE-1 and ANTIDE-3, non-cleavable linkers were used to produce covalent complexes between aminoethyl-eVB12 and ANTIDE-1 and -3, thereby separating the bulky VB12 group from the ANTIDE analogue. VB12-ANTIDE-1 conjugates formed with either an anilido (PA) or an EGS spacer, or VB12-ANTIDE-3 conjugates formed with an anilido, EGS- or DSS-derived spacer, all produced conjugates with in vitro activity similar to that of native ANTIDE (FIG. 1), suggesting that placing the VB12 group at some distance from the ANTIDE restored the affinity of the ANTIDE for its receptor. These conjugates had very low activities in vivo (FIG. 2), possibly due to the removal of the conjugates from the circulation by VB12-binding proteins, such as Transcobalamin I or Transcobalamin II, which would greatly reduce their in vivo potency.

In an attempt to reduce the possibility of steric hindrance produced by the presence of the VB12 in the conjugates, or reduced systemic bioavailability of the conjugates as a result of clearance by VB12-binding proteins, VB12-ANTIDE conjugates were prepared using linkers which were potentially biodegradable in vivo. A disulfide linkage was initially chosen, because this linkage is most readily cleaved in vivo, and is found in biological conjugates such as the A-SS-B subunit toxins, tetanus toxin and diphtheria toxin (Sandvig & Olsens, 1981; Matsuda & Yoneda, 1974). Disulfide bonds have been shown to be cleaved by the low levels of glutathione found in serum, or in the cytoplasm of cells (Anderson & Meister, 1980).

The disulfide-linked VB12-ANTIDE-1 and VB12-ANTIDE-3 conjugates were found to have a slightly reduced in vitro potency in comparison to ANTIDE, or the Anilido- and EGS-linked VB12-ANTIDE-1 and ANTIDE-3 conjugates. In contrast, the disulfide linked conjugates showed a dramatic increase in their in vivo potencies when compared to the non-cleavable, extended spacer conjugates (FIGS. 3 & 4, Tables 5 & 6). For the B12-SS-NH$^+$-ANT3 conjugate, the in vivo bio-activity slightly exceeded that of the HS-NH$^+$-ANT3 analogue. A spacer of similar length containing a non-cleavable thioether bond rather than the disulfide bond showed greatly reduced in vivo activity, suggesting that the increased activity of the disulfide linked conjugate was due to its ability to be cleaved in vivo. All conjugates described above, whether they were directly linked to VB12 or were linked by a cleavable or non-cleavable spacer were found to be significantly more soluble in physiological buffers such as PBS or saline, than the parent ANTIDE molecule (results not shown).

Conjugates between VB12 and ANTIDE-1 and -3 were formed with a spacer containing a γ-glutamyl-ε-lysine bond, which could potentially be cleaved by serum transglutaminases. Despite the high in vitro activity of these conjugates, their in vivo activity was very low, suggesting that the spacer was not cleaved in vivo.

The affinity of the VB12-ANTIDE-1 and -3 conjugates for IF was found to be equal or greater than the affinity of the eVB12 isomer from which the conjugates were made. A similar observation has been made for other eVB12 isomer conjugates (Russell-Jones, 1994)

These studies demonstrate that is is possible to link together two molecules with disparate biological activities and to substantially maintain the biological activity of each individual component. During such conjugation, care must be taken to maintain the receptor-ligand binding activity of both molecules, as well as preserving the bio-availability of the pharmacological agent. Thus, although it was possible to make several complexes between VB12 and ANTIDE using spacers while showing high in vitro activity in the pituitary cell assay, and with high relative affinity for IF, the in vivo bioactivity of these conjugates was greatly reduced. In this case, an alternative approach using biodegradable spacers to join the two molecules proved successful.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Schally, A. B., Ariumara, A., Kastin, A. J., et al., 1971 Science 173, 1036
2. Loumay, E., Naor, Z., and Catt, K. J. 1982 Endocrinol., 111, 730
3. Perrin, M. H., Rivier, J. E., and Vale, W. W. 1980 Endocrinol., 102, 1289
4. Eisenberger, M., and Abrams, J., 1988., Drugs Today, 24, 241
5. Crawford, D. D., and Davis, M. A., in "Endocrine Therapies in Breast and Prostate Cancer." (Ed) C. K. Osborne, Boston p.25.
6. Karten, M. J., and Rivier, J. E. 1986 Endocrin. Rev., 7, 44
7. Schmidt, F., et al., 1984 Contraception, 29, 283
8. Phillips, A., et al., 1988 Life Sciences 43, 883.
9. Ljundgquist, A., et al., 1988 P.N.A.S. 85, 8236
10. Leal, J. A., et al., 1988 J. Clin. Endocrinol. Metab., 67, 1325
11. Habenicht, U.-F., Schneider, M. R., Fathy El Etreby, M. 1990 J. Steroid. Biochem. Molec. Biol., 37, 397.
12. McLachlan, T. I., Healy, D. L., Burger, H. G., 1986 Brit. J. Obstet. Gynaec., 93, 431.

13. Farnworth, P. G., Robertson, D. M., de Kretser, D. M. and Burger, H. G. 1988 Effects of 31 kilodalton bovine inhibin on follicle-stimulating hormone and luteinizing hormone in rat pituitary cells in vitro: actions under basal conditions. Endocrinol., 122, 207–313.
14. Russell-Jones, G. J. (1994) Oral delivery of Therapeutic Proteins and peptides by the vitamin B12 uptake system. In "Peptide-based Drug Design: Controlling Transport and Metabolism." Ed. M. Taylor and G. Amidon, ACS Publications.
15. Sandvig, K. & Olsens, S. (1981) Rapid entry of nicked Diptheria toxin into cells at low pH. Characterization of the entry process and effects of low pH on the toxin molecule. *J. Biol. Chem.,* 256, 9068–9076.
16. Matsuda, M. & Yoneda, M (1974) Dissociation of tetanus neurotoxin into two polypeptide fragments. *Biochem. Biophys. Res. Com.,* 57, 1257–1262.
17. Anderson, M. E., & Meister, A. (1980) Dynamic state of glutathione in blood plasma. *J. Biol. Chem.,* 255, 9530–9533.

I claim:

1. A LHRH antagonist selected from the group consisting of N-Ac-D-Nal(2), D-Phe(pCl), D-Pal(3), Ser, Lys(Nic), D-Lys, Leu, Lys (iPr), Pro, D-Ala-NH$_2$; N-Ac-D-Nal(2), D-Phe(pCl), D-Pal(3), Ser, Lys, D-Lys (Nic), Leu, Lys(iPr), Pro, D-Ala-NH$_2$; N-Ac-D-Nal(2), D-Phe(pCl), D-Pal(3), Ser, Lys(Nic), D-Lys(Nic), Leu, Lys (iPr), Pro, D-Ala-NH$_2$.

2. A complex for use in chemical castration of a subject or in treatment of gonadotrophin dependent disorders the complex comprising an LHRH antagonist linked to a carrier being vitamin B12 or an analogue thereof via a linker group, the linker group being characterised in that the LHRH antagonist is cleaved from a carrier in vivo.

3. A complex as claimed in claim 2 wherein the LHRH antagonist is selected from the group consisting of ANTIDE-1, ANTIDE-2 and ANTIDE-3.

4. A complex as claimed in claim 3 wherein the LHRH antagonist is ANTIDE-3.

5. A complex as claimed in claim 2 wherein more than one LHRH antagonist is linked to the carrier.

6. A complex as claimed in claim 2 in which the carrier is selected from the group consisting of cyanocobalamin, aquocobalamin, adenosylcobalamin, methylcobalamin, hydroxycobalamin, cyanocobalamin, carbanalide, 5-o-methylbenzylcobalmin, the desdimethyl, monoethylamide and the methylamide analogues all of the above, analogues and homologues of cobamamide, coenzyme B12, 5'-deoxyadenosylcobalamine, chlorocobalamin, sulfitocobalamin, nitrocobalamin, thiocyanatocobalamin, benzimidazole derivatives, adenosylcyanocobalmin, cobalamin lactone, cobalamin lactam and the anilide, ethylamide, propionamide, monocaboxylic and dicarboxylic acid derivatives of vitamin B12 or its analogues.

7. A complex as claimed in claim 2 in which the LHRH antagonist is linked to the carrier via a thiol cleavable cross-linker.

8. A complex as claimed in claim 6 in which the LHRH antagonist is linked to the carrier by a disulphide linkage.

9. A method for chemical castration or treatment of gonadotrophin dependent disorders of a subject comprising administering to the subject an effective amount of the complex as claimed in claim 2.

10. A LHRH antagonist according to claim 1, wherein the LHRH antagonist is N-Ac-D-Nal(2), D-Phe(pCl), D-Pal(3), Ser, Lys(Nic), D-Lys, Leu, Lys (iPr), Pro, D-Ala-NH$_2$.

11. A LHRH antagonist according to claim 1, wherein the LHRH antagonist is N-Ac-D-Nal(2), D-Phe(pCl), D-Pal(3), Ser, Lys, D-Lys (Nic), Leu, Lys(iPr), Pro, D-Ala-NH$_2$.

12. A LHRH antagonist according to claim 1, wherein the LHRH antagonist is N-Ac-D-Nal(2), D-Phe(pCl), D-Pal(3), Ser, Lys(Nic), D-Lys(Nic), Leu, Lys (iPr), Pro, D-Ala-NH$_2$.

13. A complex as claimed in claim 2, wherein multiple copies of the LHRH antagonist are linked to a polymeric backbone, to which is conjugated one or more molecules of vitamin B12 or an analogue thereof.

14. A method of making a complex as claimed in claim 7, comprising:

(a) reacting vitamin B12 or an analogue thereof by reaction with a thiol cleavable cross-linking agent;

(b) introducing a free thiol group into an LHRH antagonist selected from the group consisting of N-Ac-D-Nal (2), D-Phe(pCl), D-Pal(3), Ser, Lys(Nic), D-Lys, Leu, Lys (iPr), Pro, D-Ala-NH$_2$; N-Ac-D-Nal(2), D-Phe (pCl), D-Pal(3), Ser, Lys, D-Lys (Nic), Leu, Lys(iPr), Pro, D-Ala-NH$_2$; N-Ac-D-Nal(2), D-Phe(pCl), D-Pal (3), Ser, Lys(Nic), D-Lys(Nic), Leu, Lys (iPr), Pro, D-Ala-NH$_2$; and reacting the products of (a) and (b) to produce said complex.

15. A method for chemical castration or treatment of gonadotrophin dependent disorders of a subject comprising administering to the subject an effective amount of the complex as claimed in claim 7.

* * * * *